United States Patent
Ma

(10) Patent No.: US 11,054,418 B2
(45) Date of Patent: Jul. 6, 2021

(54) SOLID-PHASE CARRIER CAPABLE OF IMPROVING DETECTION SENSITIVITY, AND DETECTION COMPONENT

(71) Applicant: SUZHOU SJ BIOMATERIALS, LTD. CO., Suzhou (CN)

(72) Inventor: Xiongming Ma, Suzhou (CN)

(73) Assignee: SUZHOU SJ BIOMATERIALS, LTD. CO., Suzhou (CN)

( * ) Notice: Subject to any disclaimer, the term of this patent is extended or adjusted under 35 U.S.C. 154(b) by 153 days.

(21) Appl. No.: 16/326,923

(22) PCT Filed: Aug. 22, 2016

(86) PCT No.: PCT/CN2016/096201
§ 371 (c)(1),
(2) Date: Feb. 21, 2019

(87) PCT Pub. No.: WO2018/035670
PCT Pub. Date: Mar. 1, 2018

(65) Prior Publication Data
US 2019/0187134 A1 Jun. 20, 2019

(51) Int. Cl.
*G01N 33/545* (2006.01)
*C08G 77/38* (2006.01)
*C12N 15/63* (2006.01)
*C08K 3/22* (2006.01)

(52) U.S. Cl.
CPC .......... *G01N 33/545* (2013.01); *C08G 77/38* (2013.01); *C08K 3/22* (2013.01); *C12N 15/63* (2013.01); *C08K 2003/2241* (2013.01); *C08K 2201/005* (2013.01)

(58) Field of Classification Search
CPC ...... G01N 33/545; C08G 77/38; C08G 77/12; C08G 77/20; C08G 77/24; C08L 83/04; C08K 2003/2241; C08K 2201/005
See application file for complete search history.

(56) References Cited

U.S. PATENT DOCUMENTS

| 6,841,645 B1 * | 1/2005 | Dromard ............... C11D 3/373 510/116 |
| 8,252,881 B2 | 8/2012 | Ma |
| 2005/0237480 A1 | 10/2005 | Allbritton et al. |
| 2012/0226001 A1 | 9/2012 | Brook et al. |

FOREIGN PATENT DOCUMENTS

| CN | 1696656 A | 11/2005 |
| CN | 101265329 A | 9/2008 |
| CN | 104098677 A | 10/2014 |
| EP | 2280311 | 2/2011 |
| EP | 2541327 | 1/2013 |
| WO | WO2006004537 A1 | 1/2006 |

OTHER PUBLICATIONS

Madaeni et al. Polymer Engineering and Science 52(12) (2012) pp. 2664-2674.*
S.S. Madaeni et al, "Effect of titanium dioxide nanoparticles on polydimethylsiloxane/polyethersulfone composite membranes for gas separation", Polymer Engineering and Science., US, (Jun. 19, 2012), vol. 52, No. 12, pp. 2664-2674, abstract; p. 2665, right-hand column, section "Preparation of nanocomposite membranes"; p. 2668, right-hand column, last paragraph.
Wu et al., J Am Chem Soc, 2007, 129, 7726-7227 A Facile Method for Permanent and Functional Surface Modification of Poly(dimethylsiloxane).

* cited by examiner

*Primary Examiner* — Kuo Liang Peng
(74) *Attorney, Agent, or Firm* — Adam Warwick Bell; Matthew Rupert Kaser

(57) ABSTRACT

Provided is a solid phase carrier capable of improving detection sensitivity, and a detection device. The solid phase carrier is provided with a polydimethylsiloxane layer with an initiator on the surface, and titanium dioxide particles distributed in said polydimethylsiloxane layer with an initiator on the surface.

9 Claims, 2 Drawing Sheets

SOLID-PHASE CARRIER CAPABLE OF IMPROVING DETECTION SENSITIVITY, AND DETECTION COMPONENT

TECHNICAL FIELD

The present invention belongs to the field of functional materials, and in particular relates to a polydimethylsiloxane solid phase carrier with an initiator on the surface, which is capable of improving detection sensitivity, and a detection device using the solid phase carrier as a substrate.

BACKGROUND ART

A polydimethylsiloxane (abbreviated as PDMS hereinafter) has excellent properties such as non-toxicity, transparency, elasticity, and chemical inertness, and has become a preferred functional material in the fields of applications including microfluidic systems, micro-electromechanical systems, soft lithography and unconventional nanolithography.

In order to utilize the functions of a PDMS-based device better and further promote the application of PDMS, it is generally necessary to perform surface modification of the PDMS.

As a surface modification technique for PDMS, Chinese Patent Publication No. CN 101265329A disclosed a polydimethylsiloxane with an initiator on the surface (initiator-integrated polydimethylsiloxane, abbreviated as iPDMS), which is a universal, permanent, diverse and functional surface-modified polydimethylsiloxane material. In particular, applying the iPDMS to the field of biological detection can prevent non-specific adsorption of proteins completely.

However, the detection sensitivity of a detection device using the above-mentioned iPDMS material as a substrate still has to be improved.

SUMMARY OF THE INVENTION

In view of the above-mentioned technical problem present in the prior art, an object of the present invention is to provide an iPDMS material-based solid phase carrier capable of improving detection sensitivity, a detection device comprising the carrier, and a detection kit.

The inventor has conducted intensive studies in order to solve the above-mentioned technical problem, and as a result, it has been found that by adding titanium dioxide particles to said iPDMS material, the detection sensitivities of the iPDMS material-based solid phase carrier, the detection device comprising the carrier, and the detection kit can be improved, thus completing the present invention.

That is, the present invention comprises:

1. A solid phase carrier provided with
a polydimethylsiloxane layer with an initiator on the surface, and
titanium dioxide particles distributed in said polydimethylsiloxane layer with an initiator on the surface.

2. The solid phase carrier according to item 1, wherein the content of said titanium dioxide particles is 0.0001 to 100 parts by weight, preferably 0.0002 to 90 parts by weight, more preferably 0.0005 to 80 parts by weight, more preferably 0.001 to 70 parts by weight, more preferably 0.002 to 60 parts by weight, more preferably 0.005 to 40 parts by weight, more preferably 0.01 to 40 parts by weight, more preferably 0.02 to 30 parts by weight, more preferably 0.05 to 20 parts by weight, and more preferably 0.1 to 10 parts by weight, relative to 100 parts by weight of said polydimethylsiloxane layer with an initiator on the surface.

3. The solid phase carrier according to item 1, wherein said titanium dioxide particles have an average particle size of 1 nm to 1000 nm, preferably 5 nm to 500 nm, more preferably 5 nm to 200 nm, more preferably 10 nm to 100 nm, and more preferably 10 nm to 50 nm.

4. The solid phase carrier according to any one of items 1-3, wherein the solid phase carrier is film-like.

5. The solid phase carrier according to any one of items 1-4, further comprising: an oligomeric ethylene glycol methacrylate layer located on said polydimethylsiloxane layer with an initiator on the surface.

6. A detection device comprising:
the solid phase carrier of item 5, and
a polypeptide or protein linked to said oligomeric ethylene glycol methacrylate layer.

7. A detection kit comprising the detection device of item 6 or the solid phase carrier of any one of items 1-5.

Effects of the Invention

According to the present invention, an iPDMS material-based solid phase carrier capable of improving detection sensitivity, a detection device comprising the carrier, and a detection kit are provided.

DETAILED DESCRIPTION OF EMBODIMENTS

Figure 1:
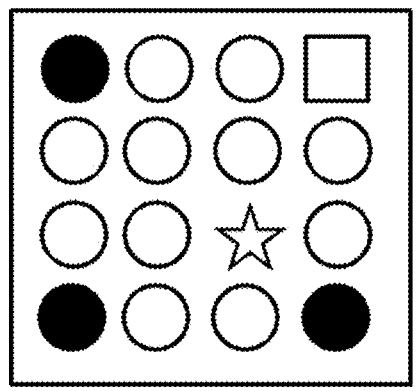
FIG. 1 is a diagram of a spotted pattern of a polypeptide microarray.

The scientific and technological terminologies referred to herein have the same meanings as what are generally understood by a person skilled in the art, and if there is a conflict, the definition in the present description shall prevail.

Firstly, in one aspect, the present invention provides a solid phase carrier (the solid phase carrier of the present invention) comprising:
a polydimethylsiloxane layer with an initiator on the surface, and
titanium dioxide particles distributed in said polydimethylsiloxane layer with an initiator on the surface.

Said polydimethylsiloxane with an initiator on the surface (iPDMS) belongs to the prior art, and reference can be made to Chinese Patent Publication No. CN 101265329 A.

Titanium dioxide, commonly known as titanium white, is usually a white powder. The crystal form of said titanium oxide is not particularly limited and may be, for example, of rutile type, anatase type or nanoscale ultrafine titanium dioxide.

Preferably, said titanium dioxide particles have an average particle size of 1 nm to 1000 nm, more preferably 5 nm to 500 nm, more preferably 5 nm to 200 nm, more preferably 10 nm to 100 nm, and more preferably 10 nm to 50 nm.

The specific surface area of said titanium dioxide particles is preferably 10 to 500 $m^2/g$, more preferably 20 to 400 $m^2/g$, more preferably 30 to 300 $m^2/g$, and more preferably 40 to 200 $m^2/g$.

The content of said titanium dioxide particles is 0.0001 to 100 parts by weight, preferably 0.0002 to 90 parts by weight, more preferably 0.0005 to 80 parts by weight, more preferably 0.001 to 70 parts by weight, more preferably 0.002 to 60 parts by weight, more preferably 0.005 to 40 parts by weight, more preferably 0.01 to 40 parts by weight, more preferably 0.02 to 30 parts by weight, more preferably 0.05 to 20 parts by weight, and more preferably 0.1 to 10 parts by weight, relative to 100 parts by weight of said polydimethylsiloxane layer with an initiator on the surface.

Said solid phase carrier may be prepared, for example, by mixing macromolecular precursor A, cross-linking agent B, vinyl-endcapped initiator C, and said titanium dioxide particles D at a certain weight ratio, and leaving the mixture to stand, for example, for 6 to 24 hours to form an elastomer. In the mixture, said macromolecular precursor A is poly (dimethyl-methylvinylsiloxane); said cross-linking agent B is vinyl-endcapped poly(dimethyl-methylvinylsiloxane) and poly(dimethyl-methylhydrogenosiloxane); and said vinyl-endcapped initiator C is 10-undecenyl 2-bromo-2-methyl-propionate.

The shape of said solid phase carrier includes, but is not limited to: beads, magnetic beads, films, microtubes, filter membranes, plates, microplates, carbon nanotubes, sensor chips, etc. Pits, grooves, filter membrane bottoms and the like may be provided on a flat solid phase carrier such as a film or a plate.

Preferably, said solid phase carrier further comprises: an oligomeric ethylene glycol methacrylate layer located on said polydimethylsiloxane layer with an initiator on the surface. Said oligomeric ethylene glycol methacrylate layer may be formed by initiating the polymerization of oligomeric ethylene glycol methacrylate on said polydimethylsiloxane layer with an initiator on the surface. Such a solid phase carrier can completely prevent non-specific adsorption of proteins.

In another aspect, the present invention provides a detection device (the detection device of the present invention) comprising: the above-mentioned solid phase carrier of the present invention, and a polypeptide or protein linked to said oligomeric ethylene glycol methacrylate layer. The manner by which said polypeptide or protein is linked to said oligomeric ethylene glycol methacrylate layer may be a covalent linkage, and reference can be made to, for example, the description of International Patent Application Publication WO 2014044184 for details. The polypeptide layer or protein herein refers to a compound obtained by the dehydration condensation of amino acid molecules, usually, the compound consisting of 2 to 50 amino acid residues is referred to as a polypeptide, and the compound consisting of 50 or more amino acid residues is referred to as a protein.

The detection device of the present invention has high detection sensitivity and can completely inhibit non-specific binding of proteins, and is thus particularly suitable for detecting a substance (e.g., a protein, a polypeptide, a small molecule compound, a nucleic acid and the like) capable of binding to the polypeptide or protein in said polypeptide layer or protein layer.

In another aspect, the present invention provides a detection kit (the detection kit of the present invention) comprising the above-mentioned detection device of the present invention or the solid phase carrier of the present invention. The detection kit of the present invention may further comprise other components, and reference can be made to, for example, the description of International Patent Application Publication WO 2014044184.

The detection kit of the present invention is also particularly suitable for detecting a substance (e.g., a protein, a polypeptide, a small molecule compound, a nucleic acid and the like) capable of binding to the polypeptide or protein in said polypeptide layer or protein layer.

Examples

The present invention will be described below in more detail by means of examples, but the present invention is not limited to these examples.

1. Preparation and Confirmation of Polypeptides

A peptide composed of 30 amino acids used in the examples has an amino acid sequence as set forth in SEQ ID NO: 1, which was synthesized by GL Biochem (Shanghai) Ltd.

SEQ ID NO: 1: PLVEDGVKQCDRYWPDE-GASLYHVYEVNLV is positive for sera of patients with type 1 diabetes, and negative for sera of normal healthy individuals or non-type 1 diabetic patients, and reference can be made to Chinese Patent Application Publication No. CN104098677A.

2. Preparation of Detection Device

Detection devices 1-4 comprising SJ-modified silica gel thin films 1-4 of the invention were obtained as described in Example 2 of Chinese Patent Application Publication No. CN 104098677 A, except that in order to prepare the SJ-modified silica gel thin films 1-4 of the invention, the polydimethylsiloxane precursor A, cross-linking agent B, vinyl-endcapped initiator C and titanium oxide particles D (with an average particle size of 40 nm, a specific surface area of 60 $m^2/g$, of rutile type) were sufficiently mixed at a ratio of A:B:C:D=10:1:0.2:(5, 1, 0.5 or 0.1), respectively.

Detection devices 5-8 comprising SJ-modified silica gel thin films 5-8 of the invention were obtained as described in Example 2 of Chinese Patent Application Publication No. CN 104098677 A, except that in order to prepare the SJ-modified silica gel thin films 5-8 of the invention, the polydimethylsiloxane precursor A, cross-linking agent B, vinyl-endcapped initiator C and titanium oxide particles D (with an average particle size of 20 nm, a specific surface area of 120 $m^2/g$, of rutile type) were sufficiently mixed at a ratio of A:B:C:D=10:1:0.2:(5, 1, 0.5 or 0.1), respectively.

In addition, a detection device of Example 2 of Chinese Patent Application Publication No. CN 104098677 A (the SJ-modified silica gel thin film used does not comprise titanium oxide particles) was prepared as a control.

3. Detection with Detection Devices

Test Steps

1. Before starting the detection, a concentrated washing solution was added to purified water or distilled water at a ratio of 1:10 for dilution, after the completion of which a washing solution was obtained for direct use, and the washing solution was added to the surface of a chip at 100 µL/well using a pipettor, and the chip was soaked for 3 minutes to ensure that the surface of the chip was completely infiltrated.

2. A serum sample to be tested was diluted with the sample dilution solution at 1:10, 1:100 or 1:1000 and mixed uniformly.

3. The washing solution in which the chip was soaked was discarded, and under the condition of the surface of the chip being completely wet, 100 μL of each serum sample was pipetted and added to a chip reactor.

4. The chip reactor was placed within a chip holder which was then placed on a shaking table, the shaking table was turned on with a frequency of 150 rpm, and incubation was carried out for 30 minutes at room temperature.

5. The serum sample in the chip reactor was discarded, and the reaction chamber body and the surface of the chip were washed with 50 mL of the washing solution 3 times.

6. After the washing was completed, 100 μL of an enzyme-labelled secondary antibody solution was added to each well of the chip reactor, the chip reactor was placed within a chip holder which was then placed on a shaking table, the shaking table was turned on with a frequency of 150 rpm, and incubation was carried out for 30 minutes at room temperature.

7. The enzyme-labelled secondary antibody solution in the chip reactor was discarded, and the reaction chamber body and the surface of the chip were washed with 50 mL of the washing solution 3 times.

8. After the washing was completed, 100 μL of a color developing solution was added to each well of the chip reactor, and after 10 minutes of color development in the dark, the result was visually observed and read.

The samples of sera of normal healthy individuals, of patients with type 1 diabetes and of patients with other diseases were provided by a cooperation hospital, and the disease criteria were all confirmed by clinical examinations, and informed consent forms had been obtained from the donors.

FIG. 1 shows a dotted pattern of a polypeptide microarray. In the pattern, the three black circular spot samples refer to human IgG, and act as location spots; the one square spot sample refers to a PB spotting solution, and acts as a blank control; and the polypeptide of the star-shaped spot sample is a polypeptide as set forth in SEQ ID NO: 1, which is a type 1 diabetic autoantigen protein polypeptide that responds to some of the sera of patients with type 1 diabetes.

The results of detection using detection devices 1-8 and the control detection device prepared according to Example 2 as mentioned above are shown as in FIGS. 2-5.

Figure 2:
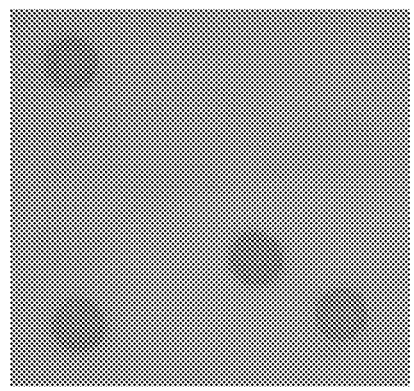
FIG. 2 is a photograph showing a detection result obtained by diluting a serum sample to be tested with a sample dilution solution at 1:10 using a control detection device.
Figure 3:
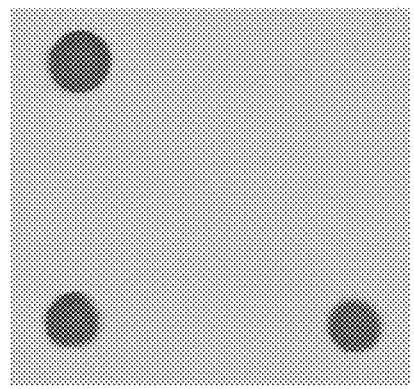
FIG. 3 is a photograph showing a detection result obtained by diluting a serum sample to be tested with a sample dilution solution at 1:100 using a control detection device.

FIG. 2 is a detection result obtained by diluting a serum sample to be tested with a sample dilution solution at 1:10 using a control detection device. FIG. 3 is a detection result obtained by diluting a serum sample to be tested with a sample dilution solution at 1:100 using a control detection device. It can be seen from FIGS. 2 and 3 mentioned above that in the case of using the control detection device, where the serum sample to be tested is diluted at 1:100, the detection result is substantially invisible upon visual observation.

Figure 4:
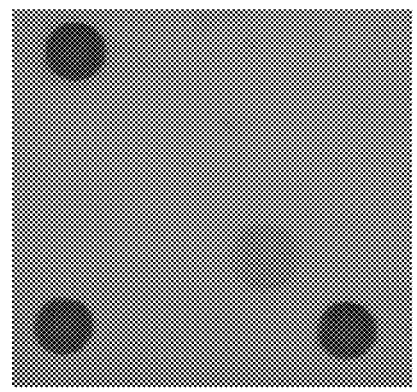
FIG. 4 is a photograph showing a detection result obtained by diluting a serum sample to be tested with a sample dilution solution at 1:1000 using a detection device 1.
Figure 5:
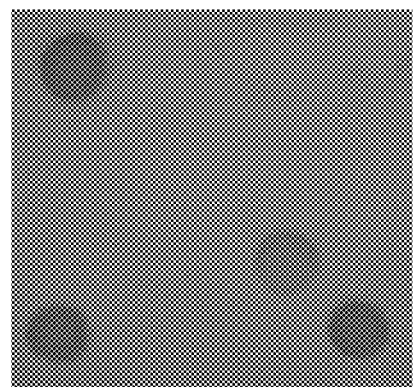
FIG. 5 is a photograph showing a detection result obtained by diluting a serum sample to be tested with a sample dilution solution at 1:1000 using a detection device 8.

In contrast, in the case of using detection devices 1-8, even though the serum sample to be tested is diluted with the sample dilution solution at 1:1000, the detection result remains clear and visible upon visual observation. As a typical case, FIG. 4 is the detection result obtained by diluting a serum sample to be tested with a sample dilution solution at 1:1000 using the detection device 1. FIG. 5 is a detection result obtained by diluting a serum sample to be tested with a sample dilution solution at 1:1000 using a detection device 8.

From the above results, it can be seen that by using the solid phase carrier of the present invention, the detection sensitivity of the detection device can be increased by at least 10 times.

The present invention has been described above by way of specific embodiments and examples, but it should be understood by a person skilled in the art that these are not intended to define the scope of the present invention and the scope of the present invention should be defined by the claims.

INDUSTRIAL APPLICABILITY

According to the present invention, an iPDMS material-based solid phase carrier capable of improving detection sensitivity, a detection device comprising the carrier, and a detection kit are provided.

The invention claimed is:

1. A solid phase carrier provided with a polydimethylsiloxane layer with an initiator on the surface, and titanium dioxide particles distributed in said polydimethylsiloxane layer with an initiator on the surface.

2. The solid phase carrier according to claim 1, wherein the content of said titanium dioxide particles is 0.0001 to 100 parts by weight relative to 100 parts by weight of said polydimethylsiloxane with an initiator on the surface.

3. The solid phase carrier according to claim 1, wherein said titanium dioxide particles have an average particle size of 1 nm to 1000 nm.

4. The solid phase carrier according to claim 1, wherein the solid phase carrier is film-like.

5. The solid phase carrier according to claim 1, wherein the content of said titanium dioxide particles is 0.001 parts or more by weight relative to 100 parts by weight of said polydimethylsiloxane with an initiator on the surface.

6. The solid phase carrier according to claim 1, wherein said titanium dioxide particles have an average particle size of 5 nm to 200 nm.

7. The solid phase carrier according to claim 1, further comprising: an oligomeric ethylene glycol methacrylate layer located on said polydimethylsiloxane layer with an initiator on the surface.

8. A detection device comprising: the solid phase carrier of claim 7, and a polypeptide or protein linked to said oligomeric ethylene glycol methacrylate layer.

9. A detection kit comprising the solid phase carrier of claim 1.

* * * * *